United States Patent [19]
Harada et al.

[11] Patent Number: 4,463,091
[45] Date of Patent: Jul. 31, 1984

[54] METHOD OF PRODUCING AMYLASE INHIBITOR AI-B

[75] Inventors: Takahiro Harada, Ube; Eiji Miyagawa, Yamaguchi; Junko Umemoto, Ube; Tsutomu Yoshida, Onoda; Toshinari Hamakado, Ube, all of Japan

[73] Assignee: Fujirebio Kabushiki Kaisha, Tokyo, Japan

[21] Appl. No.: 267,828

[22] Filed: May 28, 1981

[30] Foreign Application Priority Data

Jun. 4, 1980 [JP] Japan .................................. 55-74203

[51] Int. Cl.$^3$ ...................... C12P 21/00; C12P 21/02; C12P 21/04; C12R 1/465
[52] U.S. Cl. ......................................... 435/68; 435/70; 435/71; 435/886
[58] Field of Search ...................... 435/68, 76, 886, 71

[56] References Cited

U.S. PATENT DOCUMENTS

| 3,132,995 | 5/1964 | Berger et al. | 435/68 |
| 3,278,378 | 10/1966 | Schindler et al. | 435/68 |
| 3,316,148 | 4/1967 | Umezawa et al. | 435/68 |
| 3,944,537 | 3/1976 | Saunders et al. | 260/112 G |
| 4,010,258 | 3/1977 | Murao | 424/115 |
| 4,226,764 | 10/1980 | Oeding et al. | 260/112 R |
| 4,271,067 | 6/1981 | Belloc et al. | 260/112 R |
| 4,282,318 | 8/1981 | Oeding et al. | 435/68 |
| 4,339,436 | 7/1982 | Oeding et al. | 424/115 |

FOREIGN PATENT DOCUMENTS

| 514894 | 7/1955 | Canada | 435/886 |
| 627136 | 9/1961 | Canada | 435/71 |
| 658522 | 2/1963 | Canada | 435/70 |
| 51090 | 4/1977 | Japan | 435/70 |
| 135594 | 10/1980 | Japan | 435/68 |

OTHER PUBLICATIONS

Koba, *Further Purification of Amylase Inhibitor Produced by Streptomyces sp.*, Agr. Biol. Chem., 40(6), 1976, pp. 1167–1173.

Ohyama, *Purification and Some Properties of Amylase Inhibitor (S–AI)*, Agr. Biol. Chem., 41(11), 1977, pp. 2221–2228.

Murao et al.; in Chem. Abstr. 84:57382q (1976) from Japan Kokai 75,123,891 (1975).

Belloc et al.; in Chem. Abstr. 87:116425u (1977) from Ger. Offen. 2,702,417 (1977).

Oeding et al.; in Chem. Abstr. 89:161530 (1978) from Ger. Offen. 2,701,890 (1978).

Goto et al.; in Chem. Abstr. 83:176706n (1975) from Japan Kokai 75, 77,594 (1975).

Buchanan et al., *Bergey's Manual of Determinative Bacteriology*, 8th ed., Williams and Wilkins Co., Baltimore, (1974), p. 825.

ATCC Catalog, American Type Culture Collection, Rockville, MD, (1976) p. 175.

Aschauer et al.; Hoppe–Seyler's Z. Physiol. Chem. 362, 465 (1981).

Primary Examiner—Thomas G. Wiseman
Assistant Examiner—James Martinell
Attorney, Agent, or Firm—Flynn, Thiel, Boutell & Tanis

[57] ABSTRACT

A method of producing amylase inhibitor AI-B by cultivating an amylase inhibitor AI-B producing strain which belongs to the genus Streptomyces and isolating the amylase inhibitor AI-B from the culture.

4 Claims, 2 Drawing Figures

METHOD OF PRODUCING AMYLASE INHIBITOR AI-B

The present invention relates to a method of producing a novel amylase inhibitor with a reference code AI-B.

In general, amylase inhibitors are useful as medicines for treating hyperlipemia and diabetes mellitus, and for preventing tooth decay, since the amylase inhibitors inhibit the activity of amylase in the body, particularly, in the digestive system.

Therefore, development of an excellent amylase inhibitor is desired.

Furthermore, if salivary amylase and pancreatic amylase could be separately measured by use of amylase inhibitor during the quantitative measurement of serum amylase, which measurement is conducted for making a clinical diagnosis of acute pancreatitis, the development of such amylase inhibitor would become extremely significant in the clinical diagnosis.

After extensive and systematic studies of a great number of microorganisms, the inventors of the present invention have discovered that a strain belonging to the genus Streptomyces produces a novel amylase inhibitor. The novel amylase inhibitor was named amylase inhibitor AI-B.

The amylase inhibitor AI-B can be produced by cultivating an amylase inhibitor AI-B-producing strain which belongs to the genus Streptomyces and separating abstracting the amylase inhibitor AI-B from the culture.

Figure 2:
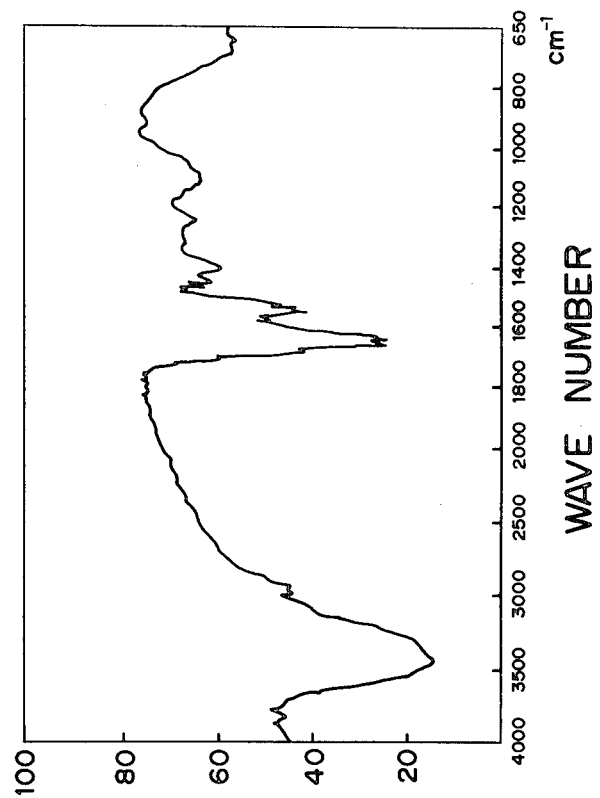
FIG. 2 is the infrared absorption spectrum of amylase inhibitor AI-B.

In the present invention, any strain belonging to the genus Streptomyces can be employed if it produces the amylase inhibitor AI-B. However, the inventors of the present invention discovered that strain No. 297-A2 is the most effective for producing the amylase inhibitor AI-B.

Since the microbiological properties of the strain No. 297-A2 are in good agreement with the properties of *Streptomyces viridosporus*, this strain has been named *Streptomyces viridosporus* No. 297-A2. A sample of this strain has been deposited at the Fermentation Research Institute, the Agency of Industrial Science and Technology, Japan, under the deposition number FERM-P No. 5405.

The microbiological characteristics of the strain *Streptomyces viridosporus* No. 297-A2 are as follows:

1. Morphological characteristics
    The spore-bearing hyphae show simple branching and form open spirals or loops in termination. The spore chains contain more than 10 spores. The spore is 0.5~0.8 μm × 1.1~15 μm in size and the surface is spiny.
2. Cultural characteristics
    (1) Sucrose—nitrate agar
        Growth (G): Moderate, Colorless
        Aerial Mycelium (AM): Moderate, Grey
        Soluble Pigment (SP): None
    (2) Glucose—asparagine agar
        G: Moderate, Colorless
        AM: Poor, White
        SP: None
    (3) Glycerin—asparagine agar
        G: Abundant, Yellowish Brown
        AM: Abundant, Greenish Grey
        SP: None
    (4) Inorganic salts—starch agar
        G: Abundant, Pale Orange
        AM: Abundant, Greenish Grey
        SP: None
    (5) Tyrosine agar
        G: Moderate, Colorless
        AM: Moderate, Grey
        SP: None
    (6) Nutrient agar
        G: Moderate, Colorless
        AM: Moderate, Light Grey
        SP: None
    (7) Yeast extract—malt extract agar
        G: Abundant, Yellowish Orange
        AM: Abundant, Greenish Grey
        SP: None
    (8) Oatmeal agar
        G: Abundant, Yellowish Orange
        AM: Abundant, Greenish Grey
        SP: None
3. Physiological Properties
    (1) Temperature range for growth
        In the yeast extract-malt agar, the amylase inhibitor AI-B producing strain grows well at temperatures ranging from 15° C. to 40° C. The optimum temperature is in the range of 25° C. to 37° C.
    (2) Liquefaction of gelatin on the glucose—peptone-gelatin medium
        The gelatin is liquefied in 21 days.
    (3) Hydrolysis of starch on starch agar: Positive
    (4) Coagulation of skim milk: Negative
    (5) Peptonization of skim milk: Positive
    (6) Reduction of nitrate: Positive
    (7) Production of melanine-like pigment
        Formation of a melanine-like pigment is not observed on the tyrosine agar, peptone-yeast extract-iron agar, or tripton-yeast extract broth.
4. Utilization of carbon sources (Pridham and Gottlieb agar) L-arabinose, D-xylose, D-glucose, D-fructose, inositol, L-rhamnose and D-manitol are utilized well, but sucrose, raffinose and cellulose are not utilized.

The properties of the strain *Streptomyces viridosporus* No. 297-A2 can be summarized as follows.

The strain belongs to the genus Streptomyces. Aerial mycelia form open spirals and the surface of the spores is spiny. The aerial mycelia show greenish-grey color on media such as starch agar and the yeast extract-malt extract agar. Further, the strain does not produce either a melanine-like pigment or a soluble pigment and does not utilize either sucrose or raffinose.

According to the descriptions of Bergey's Manual of Determinative Bacteriology (8th Edition, 1974) and the reports of the International Streptomyces Project (ISP), the International Journal of Systematic Bacteriology, Volume 22, 1972, the above observations indicate that the strain No. 297-A2 is closely related to *Streptomyces viridosporus*.

Both the strain No. 297-A2 and *Streptomyces viridosporus* as described are more specifically related with respect to the following. With respect to the morphological characteristics, the aerial mycelia are open spirals and the surface structure of the spores is spiny. With respect to the cultural characteristics, greenish grey aerial mycelia are formed on the starch agar, the yeast extract-malt extract agar, and the glycerol—asparagine agar. Furthermore, with respect to the physiological properties, a melanine-like pigment and a soluble pigment are not produced, and sucrose and raffinose cannot be utilized. From these facts, the strain No. 297-A2 has been identified as *Streptomyces viridosporus* No. 297-A2.

Physicochemical properties of the amylase inhibitor AI-B according to the present invention are as follows:

1. Effect
   Inhibits the activity of pancreatic amylase, but inhibition of the activities of salivary amylase, bacterial α-amylase, gluco-amylase and malt β-amylase is slight.
2. Stability
   pH stability: Stable in the pH ranges of 5.5 to 10.0 at 37° C. for 1 hour.
   Temperature stability: When treated in a 0.1M sodium phosphate buffer (pH 7.0) at 70° C. for 30 minutes, more than 80% of the activity of the amylase inhibitor AI-B is retained.
3. Molecular weight
   The molecular weight of the amylase inhibitor AI-B determined by gel filtration on Sephadex G-75 is 8,000.
4. Other Properties
   Neutral polypeptide having a pI value of 6.7 and no sugar.
5. Measurement of inhibitory activity of amylase inhibitor AI-B
   The amylase inhibitory activity of the amylase inhibitor AI-B is determined by using a unit of measurement of inhibitory activity which is based on the amount of the amylase inhibitor necessary for inhibiting the activity of 50% of two units of hog pancreatic amylase.
   The activity of amylase can be measured by the following procedure:
   0.5 ml of distilled water is added to 0.5 ml of a diluted enzyme liquid containing amylase to be tested. The mixture is preincubated at 37° C. for 5 minutes, followed by addition of 2 ml of a 1.5% soluble starch aqueous solution thereto. The mixture is allowed to react at 37° C. for 10 minutes. By addition of 5 ml of 0.5N hydrochloric acid to the reaction mixture with stirring, the reaction is terminated. To 0.3 ml of this solution is added 3 ml of an iodine solution comprising 0.005 wt.% of iodine and 0.05 wt.% of potassium iodide. The mixture is stirred. The absorbance [C] of the thus prepared solution at 660 nm is measured. Then, in the above-described procedure, the diluted enzyme liquid is replaced with distilled water to prepare a standard solution and the absorbance [B] of that solution is measured. The activity of amylase is defined to be one unit when $$\frac{[B] - [C]}{[B]} = 0.4.$$

When the inhibitory activity of the amylase inhibitor is measured, in the above-described procedure, instead of 0.5 ml of distilled water, diluted amylase inhibitor liquid is added to 0.5 ml of the diluted enzyme liquid. Thereafter, the same procedure is followed and the absorbance [T] of the obtained solution is measured.

It can therefore be said that the activity of amylase free from the amylase inhibitor, [A], is $([B]-[C])/[B]$, while the inhibition percentage [I] when the amylase inhibitor is present is given as follows:

$$[I] = \frac{[T] - [C]}{[B] - [C]} \times 100$$

The inhibitory activity of the amylase inhibitor is given as follows:

$$\frac{[A]}{0.8} \times \frac{[I]}{50} \times \text{Dilution Ratio of Inhibitor}$$

Figure 1:
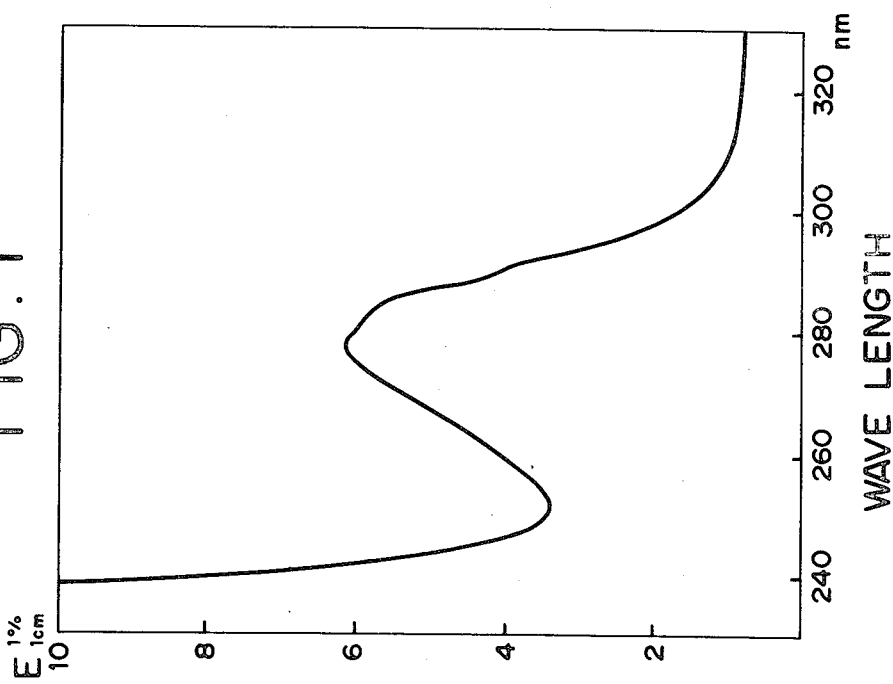
FIG. 1 is the ultraviolet absorption spectrum of amylase inhibitor AI-B.

6. Inactivation
   Entirely inactivation when treated in the pH range below 4.0 at 37° C. for 1 hour, and also when subjected to heat treatment in a 0.1M sodium phosphate buffer (pH 7.0) at 100° C. for 30 minutes.
7. Color reaction
   Colored blue by Copper-Folin method
8. Inactivating agents
   Not inactivated by addition of 1 mM of any of the following agents:
   2-mercaptoethanol, sodium ethylenediaminetetraacetate, p-chloromercuribenzoate, monoiodoacetic acid, o-phenanthroline and 8-hydroxyquinoline.
9. Inhibitory performance
   Does not inhibit trypsin, d-chymotrypsin, pepsin, alcohol dehydrogenase, malate dehydrogenase, cholesterol oxidase, alkaline phosphatase or lipase.
10. Ultraviolet absorption spectrum
    As shown in FIG. 1, the maximum ultraviolet absorption is at 278 nm, while the minimum ultraviolet absorption is at 252 nm.
11. Infrared absorption spectrum
    The infrared absorption spectrum is shown in FIG. 2.
12. Acrylamide gel disc electrophoresis
    Acrylamide gel disc electrophoresis was conducted in accordance with Davis' Method (Amn. N.Y. Acad. Sci., 121, 404, 1964), using a standard gel, and a 50 mM tris glycine buffer (pH 8.3), with a constant current of 3 mA per column.
    The result was that the realative mobility (Rm) of the amylase inhibitor AI-B to Bromophenol Blue was 0.65.

The above-mentioned physicochemical properties of the amylase inhibitor AI-B show that the amylase inhibitor AI-B is a novel amylase inhibitor, which is entirely different from the conventional amylase inhibitors derived from plants or microorganisms. In particular, the amylase inhibitor AI-B is specific in its ability to inhibit only the activity of pancreatic amylase and is therefore useful for fractional quantitative measurement of salivary amylase and pancreatic amylase in the course of quantitative measurement of serum amylase.

The amylase inhibitor AI-B according to the present invention can be produced by cultivating a strain, belonging to the genus Streptomyces, capable of producing the amylase inhibitor AI-B in a culture medium in accordance with conventional procedures.

As the nitrogen sources in the culture medium, polypeptone, meat extract and soybean meal can be employed. Further, as the carbon sources, starch, glucose, glycerine and dextrin can be employed. Sodium chloride, potassium dihydrogen phosphate, dipotassium hydrogen phosphate and magnesium sulfate can be used as inorganic salts.

In the culture media with the compositions shown in the following table, Streptomyces viridosporus No. 297-A2 was cultured with shaking at the temperatures described below in order to investigate the capability of producing the amylase inhibitor AI-B in each culture medium.

This culture shaking was conducted at temperatures ranging of 27° C. to 29° C., with a 500 ml Erlenmeyer flask containing 100 ml of each culture medium on a rotary shaker at 200 rpm.

The base culture medium contained 1.0% of polypeptone, 0.5% of soybean meal, 0.1% of sodium chloride, 0.1% of dipotassium hydrogen phosphate and 0.05% of magnesium sulfate, and the pH of the base culture medium was 7.0. The production of the amylase inhibitor AI-B began to be observed from the second day of the culture.

The results of the culture are as follows:

| Compositions of Culture Medium (with the carbon sources shown below) Carbon Source | Duration of Culture | | |
|---|---|---|---|
| | 2nd Day Inhibitory Activity (U/ml) | 3rd Day Inhibitory Activity (U/ml) | 4th Day Inhibitory Activity (U/ml) |
| 2.0% of Starch | 12.5 | 23.0 | 36.6 |
| 1% of Starch + 1.0% of Glucose | 8.0 | 10.5 | 12.3 |
| 2.0% of Glucose | 3.0 | 2.6 | 2.5 |

The above-mentioned results show that starch is a good carbon source for the amylase inhibitor AI-B. The amylase inhibitor AI-B can be produced by tank culture as well as by shaking culture. For example, 30 l of a culture medium comprising 1.0% of starch, 1.0% of polypeptone, 0.5% of soybean meal, 0.1% of sodium chloride and 0.1% of dipotassium hydrogen phosphate, with pH 7.0 is placed in a 50 l jar fermentor and is then sterilized. In this culture medium, the amylase inhibitor AI-B producing strain is cultured under the conditions of 200 rpm and 0.4 vvm at a temperature of from 27° C. to 29° C. Within a period of 42 hours to 72 hours, the production rate of the amylase inhibitor AI-B reaches a maximum.

The culture thus obtained is centrifuged to remove cells therefrom. The supernatant is then salted out by ammonium sulfate with a saturation of more than 0.5. Precipitates thus obtained by salting-out are dialyzed overnight against a 0.01M sodium phosphate buffer (pH 5.5 to 7.0). The dialyzed liquid is adsorbed to a basic ion exchange cellulose and a weakly acidic ion exchange cellulose and the active portions are eluted with sodium phosphate buffer containing sodium chloride and are then subjected to gel filtration on a Sephadex G-50. The eluted active portion is collected and lyophilized.

The following is an example in accordance with the above-described procedure.

30 l of a culture medium comprising 1.0% of starch, 1.0% of polypeptone, 0.5% of soybean meal, 0.3% of sodium chloride and 0.1% of dipotassium hydrogen phosphate, with pH 7.0, was placed in a 50 l jar fermentor, sterilized at 120° C. for 20 minutes and then cooled.

100 ml of a culture medium with the same composition as that of the above-described culture medium was placed in a 500 ml Erlenmyer flask and Streptomyces viridosporus No. 297-A2 (deposited at the Fermentation Research Institute, the Agency of Industrial Science and Technology, Japan, under the accession number FERM-P No. 5405) was inoculated to the culture medium. The inoculum was cultivated at 28° C. for 24 hours.

600 ml of the thus prepared seed culture was added to the first mentioned culture medium and cultivation was conducted under the conditions of 200 rpm and 0.4 vvm at 28° C. for 48 hours. At the end of that period, bacterial cells were removed from 30 l of the culture liquid by suction filtration. The filtrate was salted out by addition of ammonium sulfate thereto. The precipitates were collected by centrifugation and dialyzed overnight against 0.001M sodium phosphate buffer (pH 7.0). The dialyzed liquid was adsorbed to diethylaminoethyl cellulose and the active portion was eluted with a 0.01M sodium phosphate buffer containing 0.1M sodium chloride. The eluted active portion was concentrated by ultrafiltration and was then lyophilized, whereby 1.2 g of crude amylase inhibitor AI-B was obtained. This crude amylase inhibitor AI-B was dissolved in a 0.01M sodium phosphate buffer solution (pH 5.5) and was then adsorbed to carboxymethyl cellulose. The adsorbed amylase inhibitor AI-B was eluted with the same buffer containing sodium chloride with a gradient of 0M to 0.5M. The active portion was collected and then concentrated by ultrafiltration. The concentrate was subjected to gel filtration on Sephadex G-50 and was then lyophilized, whereby 150 mg of pure amylase inhibitor AI-B of 2,500 U/mg was obtained.

What is claimed is:

1. A method of producing an amylase inhibitor, designated AI-B, having the characteristics:
   (a) said inhibitor AI-B is a neutral polypeptide having an approximate molecular weight of 8,000, a pI value of 6.7 and contains no sugar;
   (b) said inhibitor AI-B inhibits the activity of pancreatic amylase, but only slightly inhibits the activities of salivary amylase, bacterial α-amylase, glucoamylase and malt β-amylase; and
   (c) said inhibitor has an ultraviolet absorption maximum at 278 nm and an ultraviolet absorption minimum at 252 nm;

comprising the steps of cultivating Streptomyces viridosporus No. 297-A2, FERM-P No. 5405 in a culture medium containing nitrogen and carbon sources assimilable and digestable by said Streptomyces viridosporus No. 297-A2, FERM-P No. 5405, until said inhibitor AI-B is substantially accumulated in said culture medium; and then recovering said accumulated inhibitor AI-B.

2. A method as claimed in claim 1, wherein said nitrogen source is at least one member selected from the group consisting of polypeptone, meat extract and soybean meal, said carbon source is at least one member selected from the group consisting of starch, glucose, glycerine and dextrin, and said culture medium further contains at least one inorganic salt selected from the group consisting of sodium chloride, potassium dihydrogen phosphate, dipotassium hydrogen phosphate and magnesium sulfate.

3. A method as claimed in claim 1, wherein said carbon source is starch.

4. A method according to claim 1, wherein said accumulated inhibitor AI-B is recovered by:
centrifuging the obtained culture of said strain to remove cells therefrom;
then salting out a supernatant obtained by said centrifugation;
then dialyzing precipitates produced by said salting out of said supernatant;
then subjecting thus-produced dialyzed liquid to a basic ion exchange cellulose and then a weakly acidic ion exchange cellulose;
then eluting active portions produced by said ion exchange steps with a salt-containing buffer;
then subjecting said liquid to gel filtration; and
then collecting and lyophilizing an active portion eluted from said gel filtration.

* * * * *